(12) United States Patent
Ziegler et al.

(10) Patent No.: US 6,857,427 B2
(45) Date of Patent: Feb. 22, 2005

(54) INTERACTIVE CHARACTER FOR USE WITH AN AEROSOL MEDICATION DELIVERY SYSTEM

(75) Inventors: Lauren R. Ziegler, Montville, NJ (US); Dirk Von Hollen, Clark, NJ (US)

(73) Assignee: RIC Investments, Inc., Wilmington, DE (US)

( * ) Notice: Subject to any disclaimer, the term of this patent is extended or adjusted under 35 U.S.C. 154(b) by 0 days.

(21) Appl. No.: 10/645,241

(22) Filed: Aug. 21, 2003

(65) Prior Publication Data

US 2004/0084045 A1 May 6, 2004

Related U.S. Application Data

(60) Provisional application No. 60/408,176, filed on Sep. 4, 2002.

(51) Int. Cl.[7] .............................................. A61M 11/00
(52) U.S. Cl. .............................. 128/200.23; 128/205.23
(58) Field of Search ....................... 128/200.11, 200.12, 128/200.14, 200.23, 203.15, 203.12, 203.16, 203.19, 200.16, 203.21, 205.23; 239/102.1, 102.2; 222/23, 39, 78; 221/24, 210, 220, 224, 226, 229; 116/200, 202

(56) References Cited

U.S. PATENT DOCUMENTS

| | | | | |
|---|---|---|---|---|
| 2,117,370 A | * | 5/1938 | Sigg ............................ 221/188 |
| 4,311,251 A | * | 1/1982 | Sternberg .................... 221/24 |
| 4,470,412 A | | 9/1984 | Nowacki et al. |
| 4,809,692 A | | 3/1989 | Nowacki et al. |
| 4,817,822 A | * | 4/1989 | Rand et al. ..................... 222/38 |
| 5,012,803 A | | 5/1991 | Foley et al. |
| 5,042,467 A | | 8/1991 | Foley |
| 5,165,392 A | | 11/1992 | Small, Jr. |
| 5,172,863 A | * | 12/1992 | Melone et al. ............... 239/211 |
| 5,301,836 A | * | 4/1994 | Luu ............................. 222/78 |
| 5,456,626 A | * | 10/1995 | Ming-Kang ................. 446/397 |
| 5,482,030 A | | 1/1996 | Klein |
| 5,779,095 A | * | 7/1998 | Diamond ..................... 221/263 |
| 5,799,651 A | * | 9/1998 | Garby et al. ........... 128/200.23 |
| 5,848,588 A | | 12/1998 | Foley et al. |
| 6,026,807 A | * | 2/2000 | Puderbaugh et al. .... 128/200.23 |
| 6,138,669 A | | 10/2000 | Rocci, Jr. et al. |
| 6,267,639 B1 | * | 7/2001 | Menow et al. ................. 446/81 |
| 6,293,279 B1 | | 9/2001 | Schmidt et al. |
| 6,360,739 B1 | | 3/2002 | Rand et al. |
| 6,425,495 B1 | * | 7/2002 | Senda et al. ................... 221/24 |
| 6,543,639 B1 | * | 4/2003 | Kovens ....................... 221/24 |
| 6,708,688 B1 | * | 3/2004 | Rubin et al. ........... 128/200.23 |

* cited by examiner

*Primary Examiner*—Henry Bennett
*Assistant Examiner*—Teena Mitchell
(74) *Attorney, Agent, or Firm*—Timothy A. Nathan; Michael W. Haas

(57) ABSTRACT

An interactive character associated with a metered dose inhaler that includes a medication dispensing canister and a canister holder. The interactive character includes a base portion adapted to be coupled to a canister such that actuation of the canister to dispense a medication requires providing an actuating force on the base portion. An interactive element is coupled to the base portion so that it that activates in a manner that is readily perceived by humans. The interactive element is actuated by an actuating system responsive to the actuating force being applied to the base portion to actuate the canister.

26 Claims, 5 Drawing Sheets

INTERACTIVE CHARACTER FOR USE WITH AN AEROSOL MEDICATION DELIVERY SYSTEM

BACKGROUND OF THE INVENTION

1. Field of the Invention

The present invention pertains to an aerosol medication delivery system, and, in particular, to an interactive character for use in an aerosol medication delivery system, wherein the interactive character operates in conjunction with a metered dose inhaler ("MDI") to encourage proper use of the system, and to a method of using such an interactive character with an MDI.

2. Description of the Related Art

It is well known to deliver a medication to a patient's respiratory system to treat a medical condition using an aerosol medication delivery system. For example, a patient suffering from an acute asthmatic attack may use an aerosol medication delivery system to deliver a bronchodilator, such as albuterol (salbutamol), in the form of a fine mist to the patient's respiratory system.

One conventional aerosol medication delivery system consists primarily of a metered dose inhaler ("MDI") and may include optional accessory devices, such as a spacer and mask. A conventional MDI, also known as simply an "inhaler", includes two components. The first component is a canister, usually made of metal, that contains the medication under pressure in a suspension or solution form and a propellant gas. The canister includes a valve and dispensing nozzle associated with the valve that delivers a fixed quantity or dose of medication each time the nozzle is depressed to actuate the valve.

The second component of an MDI is a canister holder, which typically includes a plastic tubular sleeve that holds the canister and a receptacle for the canister nozzle, which is used to hold the canister nozzle and actuate the canister valve to dispense the medication from the canister each time the canister nozzle is pushed against the receptacle on the canister holder housing. The canister holder also serves as a mouthpiece to communicate the aerosolized medication into the airway of the user or as a conduit to direct the medication into a spacer. It is also known to provide a mask at the end of the spacer opposite the MDI so that the patient can breath through his or her mouth to receive the medication.

Although unfortunate, oftentimes those who suffer from asthma and require the use of MDIs to treat asthma attacks are children. However, children, especially young children, can have difficulty synchronizing their inspiratory effort with the dispensing of medication from the MDI. That is, the optimal delivery of the aerosolized drug to the patient's respiratory system occurs if the patient inhales and holds the deep breath at the same time the medicine is dispensed from the MDI. Children using conventional aerosol medication delivery systems, however, can have difficulty understanding that they should breathe in at the same time that the medicine is being dispensed from the MDI or can have difficulty timing their inspiratory effort with the actuation of the MDI, which occurs when the child or parent applies an actuating force on the canister so that the canister nozzle is depressed against the canister holder. As a result, these patients may not achieve the optical drug delivery during use of the MDI.

SUMMARY OF THE INVENTION

Accordingly, it is an object of the present invention to provide an aerosol delivery system that overcomes the shortcomings of conventional aerosol delivery systems to provide a system that allows a pediatric patient to better coordinate his or her respiratory effort with the dispensing of drugs from the MDI. This object is achieved according to one embodiment of the present invention by providing an aerosol delivery system that includes an interactive character associated with a MDI. The interactive character includes a base portion that is adapted to be coupled to the canister such that actuation of the canister to dispense a medication requires providing an actuating force on the base portion of the interactive character. The interactive character also includes an interactive element coupled to the base portion that activates in a human perceivable manner. An actuating assembly is provided with the interactive character that actuates the interactive element when the actuating force is applied to the base portion to actuate the canister. Using this system, the child breathes in when he or she perceives the activation of the interactive element, thereby coordinating their respiratory efforts with the dispensing of the medication.

It is yet another object of the present invention to provide a method of using an aerosol delivery system that does not suffer from the disadvantages associated with conventional aerosol delivery techniques, so that a pediatric patient can better coordinate his or her respiratory effort with the dispensing of drugs from the MDI. This object is achieved by providing a method that includes coupling a base portion of an interactive character to a canister in a MDI, applying an actuating force on the base portion, and automatically activating an interactive element coupled to the base portion in a human perceivable manner responsive to the application of the actuating force on the base portion. In this way, the child breathes in when he or she perceives the activation of the interactive element, thereby coordinating their respiratory efforts with the dispensing of the medication.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
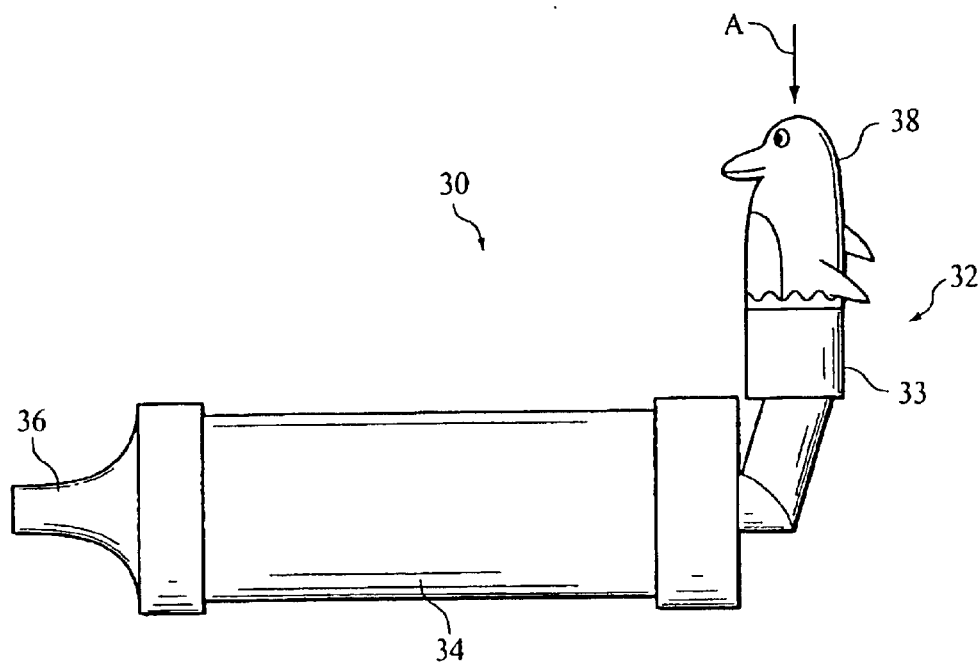
FIG. 1 is a side view of an aerosol medication delivery system including an MDI, a spacer, and an interactive character according to the principles of the present invention.

FIG. 1 illustrates an exemplary embodiment of an aerosol medication delivery system 30 according to the principles of the present invention. In the illustrated exemplary embodiment, aerosol medication delivery system 30 includes an MDI, generally indicated at 32, which includes a canister (not shown) and a canister holder/actuator or boot 33. System 30 also includes a spacer 34 having a mouthpiece 36 and an interactive character 38. FIG. 1 illustrates how the interactive character of the present invention operates in conjunction with components of the aerosol medication delivery system.

Interactive character 38 is located on the canister in the MDI, as described in greater detail below. The user actuates the canister to dispense a predetermined amount of aerosolized medication into spacer 34 by applying an actuating force on interactive character 38, as indicated by arrow A, rather than on the canister, as would be the case in a conventional MDI system. The actuating force is translated to the canister to actuate the canister in the conventional manner, so that a predetermined/metered dose of medicine is dispensed from the MDI. In addition, the actuating force is translated to interactive character 38 to cause the interactive character to perform some action that is readily perceived by the user and which indicates that the MDI system has been actuated.

For example, the present invention contemplates that interactive character 38 opens its mouth automatically when the actuating force is applied to the interactive character causing the medication to be dispensed from the canister. In this manner, the user can easily determine that it is the correct time to breathe in and hold their breath simply by observing the action of the interactive character, i.e., the opening of its mouth. Thus, the interactive character provided a clearly discernable and easily understood indication that prompts the user to breathe in synchronization with the dispensing of medication from the MDI so that the medication is taken into the patient's respiratory system in an optimal manner.

Figure 2:
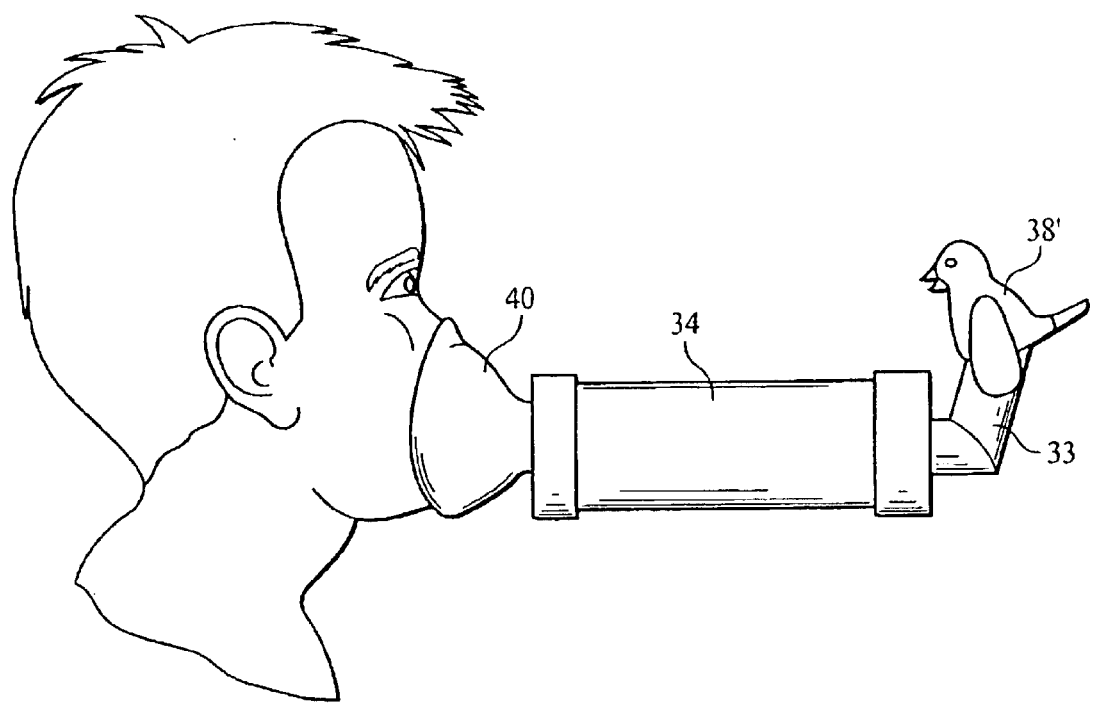
FIG. 2 is a side view an aerosol medication delivery system including an MDI, spacer, mask and a second embodiment of an interactive character according to the present invention and showing the use of the aerosol medication delivery system by a patient.

FIG. 2 is similar to FIG. 1, except that mouthpiece 36 has been replaced with a mask 40. Mask 40 functions as a patient interface device to communicate the aerosolized medication to the patient's respiratory system. In addition, interactive character 38' in FIG. 2 has an different external appearance than the interactive character of FIG. 1. It is to be understood, however, that the present invention contemplates that the interactive character can have a wide variety of external appearances, so long as the underlying function, i.e., to automatically actuate some component of the interactive character in a human perceivable format in conjunction with the dispensing of medication from the MDI, is accomplished.

It should also be understood that interactive component 38 can be used with the MDI alone, i.e., without the spacer or mask. On the other hand, the present invention also contemplates that the interactive character can be used with other accessories typically used with an aerosol medication or dry powder medication delivery system, such as a dose counter.

Figure 3A:
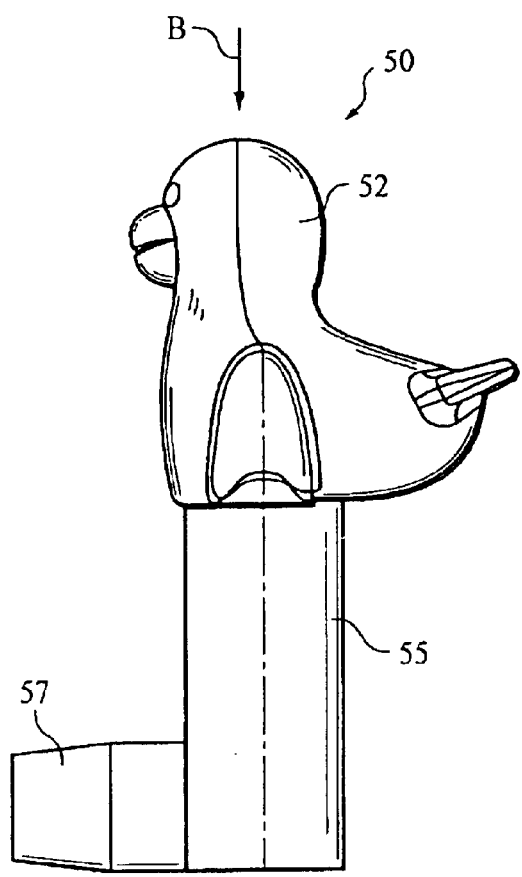
FIG. 3A is a side view of an interactive character according to the present invention showing the character in a non-actuated position.
Figure 3B:
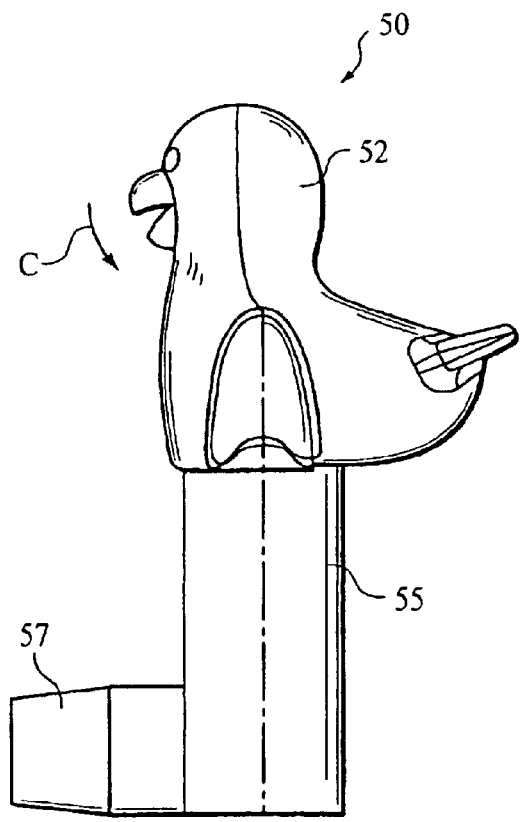
FIG. 3B is a side view of the interactive character of FIG. 3A showing the character in an actuated position.
Figure 4A:
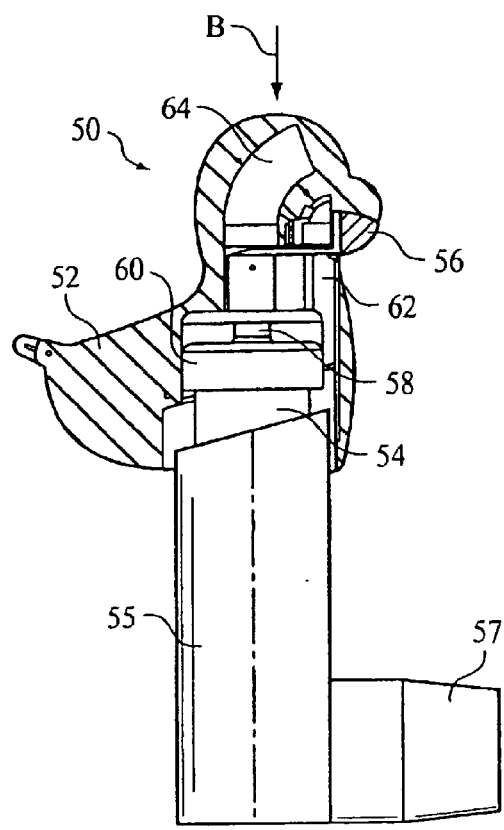
FIG. 4A is a side view, partially in section, of the interactive character of FIG. 3A.
Figure 4B:
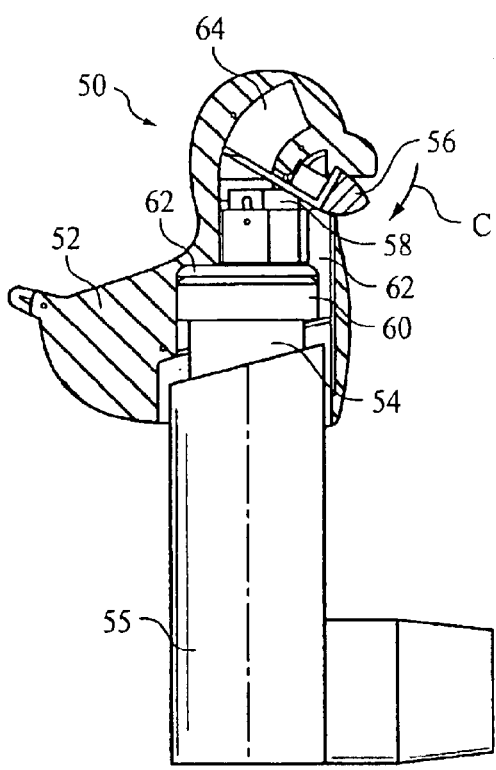
FIG. 4B is a side view, partially in section, of the interactive character of FIG. 3B.
Figure 5A:
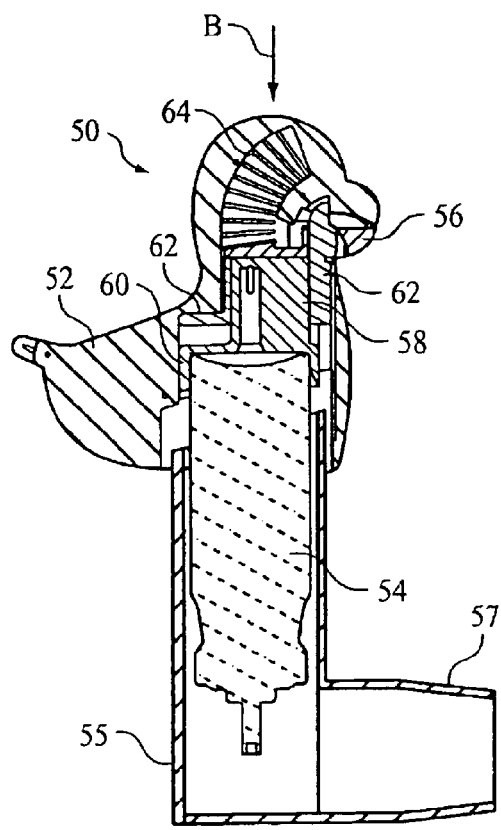
FIG. 5A is a side sectional view of the interactive character of FIG. 3A.
Figure 5B:
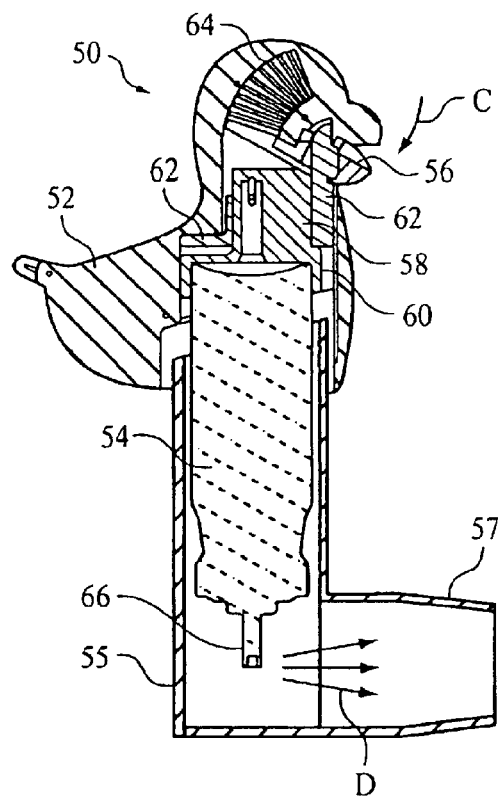
FIG. 5B is a side sectional view of the interactive character of FIG. 3B.

FIGS. 3A-5B illustrate the operation of the interactive character as well as the operating components of an exemplary embodiment of this device. FIGS. 3A-5B show an interactive character 50 having yet another external configuration that is different from those shown in FIGS. 1 and 2. In FIGS. 3A, 4A, and 5A, the interactive character is shown in a non-actuated position. While in FIGS. 3B, 4B and 5B the character is shown in an actuated position.

In this illustrated exemplary embodiment, the anatomical feature of the character that actuates when an actuating force, as indicated by arrow B, is applied to the character, is the mouth, and more specifically, the lower jaw. In other words, the character automatically opens its mouth by causing the lower jaw to move downward, as indicated by arrow C, when the actuating force (arrow B) is applied to the character. This actuating force is also translated to the canister portion of the MDI, causing a predetermined amount of medication to be dispensed, as indicated by arrows D. Once the actuating force is removed, the anatomical feature of the interactive character automatically returns to its non-actuated position.

Interactive active character 50 includes a base portion 52 that is coupled to a canister 54 in a conventional MDI system, which includes canister 54 and a canister holder 55. Base portion 52 is coupled to canister 54 such that actuation of the canister to dispense a medication requires providing an actuating force on the base portion. In this embodiment, the base portion also defines the external features of the character, such as its body, head, limbs, etc. An interactive element 56 is coupled to the based portion so that it activates or moves in a manner that can be readily perceived by a human. In the illustrated embodiment, for example, interactive element 56 is the lower jaw or beak of the bird-like character, which is moved by an actuating system to simulate opening and closing of the character's mouth.

Base portion 52 includes a hollow interior chamber that houses the components of the actuating system. The actuating system provides a mechanical linkage between the canister, the interactive element, and the base portion for moving the interactive element when the actuating force is applied to the base portion. The actuating system includes a pushrod 58 that is coupled to canister 54 by means of a canister cap 60, which is sized and configured to releasably attached to the end of the canister. Canister cap 60 and pushrod 58 slide within a channel defined in base portion 52. Interactive element 56 is located at an opposite end of the channel and is moveably positioned with respect to base portion 52 by means of a holding plate 62. Pushrod 60 engages a portion of the interactive element to cause it to move to the actuated position. A spring 64 provides a biasing force on one end of interactive element 56. This biasing force opposes the force applied by the pushrod. As a result, the interactive element is always urged toward its non-activated position, so that when the actuating force is released, the interactive character closes its mouth.

The following is a brief discussion of the use interactive character in the aerosol medication delivery system of the present invention. The MDI is prepared by placing canister 54 into canister holder 55. It should be noted that canister 54 and canister holder 55 can be any conventional MDI device. On the other hand, they may be specifically designed to form part of the interactive character of the present invention. That is, the canister holder can be designed such that the canister holder itself defines some or all of the features of the interactive character. For example, the canister holder can define the animal's legs and the interactive element can define the animal's upper body, assuming that the interactive character is an animal. In this way, when all of the elements of the system are combined, they form the entire character—complete with an interactive component. Moreover, the interactive element can be provided on the canister holder, so long as a mechanical or electrical linkage is provided to actuate the interactive element on the canister holder.

Interactive character 50 is then placed on the exposed end of canister 54. The user then places a mouthpiece portion 57 of canister holder 55 in his or her mouth, and applies an actuating force (arrow B) on the base portion. It can be appreciated that the only way to apply the actuating force on the canister is to press down on the base portion, because base portion 52 substantially covers canister 54. It should also be noted that the canister holder is maintained in a relatively fixed position while the actuating force is applied to the based portion. For example, the user typically pinches the based portion and the canister holder between their thumb and forefinger. As a result, cap 60 and pushrod 58 move upward within the channel defined in the base portion and push on an end of interactive element 56 causing it to move.

In the illustrated exemplary embodiment, this movement is a rotational movement, as indicated by arrow C, relative to plate 62 and base portion 52 to simulate opening of the character's mouth. The present invention, however, contemplates that an almost infinite amount of different variations of movements for the interactive element can be accomplished by the techniques of the present invention. In addition, multiple interactive elements can be provided so that further types of character movement are possible, such as flapping of wings, wiggling of ears, opening or closing of eyes, and movement of arms, legs, tail, head, torso, etc.

The amount of movement of pushrod 58 and cap 60 within the channel in the base portion is limited, so that once the pushrod and/or cap reach the end of channel, the continued application of the actuating force will cause the actuating force to push down in the canister. This, in turn, causes the valve in the canister to actuate in any conventional manner, thereby dispensing a predetermined dose of medication from nozzle 66. In this manner, the opening of the character's mouth occurs at or very close in time to the actual dispensing of medication from the canister. It can be appreciated that the bias force set by spring 66 and the force required to operate the canister can be made to be relatively the same, so that action of the canister and movement of the interactive element occur substantially simultaneously. The opening of the character's mouth provides a clear and easily understood indication that the user should now inhale, thereby correctly taking the medication into his or her respiratory system.

The user continues to apply the actuating force on the interactive character and inhale until the medication delivery is automatically discontinued, as occurs in a conventional MDI. Once delivery of the medication ends, the user ceases to apply the actuating force. At which time, spring 64 pushes on the end of the interactive element, moving it to its non-activated position and moving the pushrod and cap back to their starting position. In this manner, the user sees the character close its mouth and understands that this means that they can stop breathing in or holding their breath.

It can be appreciated that the present invention provides a user-friendly system and method for indicating to the user when the MDI has been actuated. Moreover, by providing this indication in the form of a child-pleasing character having an anatomical feature that moves in conjunction with the actuation of the MDI, the interactive character of the present invention is particularly well suited for pediatric use to encourage the patient to perform the best possible inspiratory technique for maximizing drug delivery. An additional benefit of the interactive character is that the friendly-faced character provides a distraction that calms the child during a distressed situation, such as an asthma attack. Its pleasing, child-friendly features allow the child to focus on the face of the animal or other character so that they can use the inhaler correctly without pulling it out of their mouth.

In the embodiment described above and shown in the figures, the interactive element of the character is an anatomical feature, such as the mouth or a portion of the mouth. It is to be understood, however, that the present invention contemplates other techniques for automatically indicating the actuation of the MDI. For example, the interactive element can be a light that changes from an deactivated state, in which light is not produced, to an activated state in which light is produced, responsive to actuation by the actuating system. Of course, in this embodiment, the actuating system can be a simple electrical contact or other conventional electric circuit with a switch to activate and deactivate the light.

In yet another embodiment, the interactive element is a sound generating element that changes from a deactivated state, in which no sound is produced, to an activated state, in which sound is produced, responsive to actuation by the actuating system. This embodiment is particularly well suited for patient's suffering from an optical disorder who may not be able to visually perceive the actuation of the interactive character.

Figure 6:
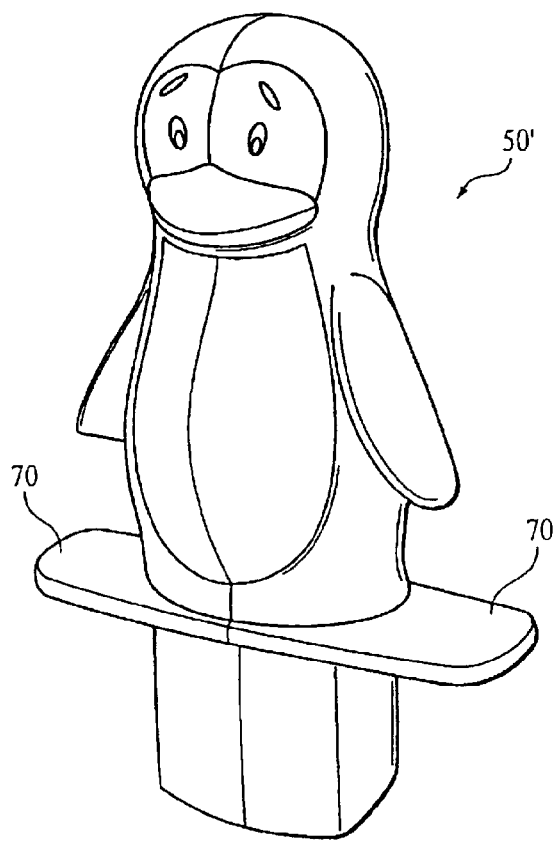
FIGS. 6 and 7 are perspective views of alternative embodiments for the interactive character according to the principles of the present invention.
Figure 7:

As alluded to above, those skilled in the art can appreciate that the base portion can have a variety of configurations. For example, the interactive character can be made to resemble an animal, a cartoon character, or any other persona or object. FIGS. 6 and 7 are provided to illustrate examples of alternative embodiments for the interactive character 50' and 50" according to the principles of the present invention. The base portion of interactive character 50' and 50" also include a pair of grasping members 70 and 72 disposed on either side of the base portion. The grasping members provide convenient places for a user to place his or her fingers for applying the actuating force on the base portion.

The present invention also contemplates that the base portion can be a mounting member, rather than define the actual exterior of the interactive character. Any one of a variety of different shapes and sizes of characters can then be selectively provided on this mounting member. This embodiment allows one universal mounting member to fit onto the canister, and a host of different characters to be placed on the mounting member. This provides flexibility in selecting which character is to be used with the MDI, without requiring that the actuating system be reproduced for each different character body.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An interactive character associated with a metered dose inhaler that includes a medication dispensing canister and a canister holder, the interactive character comprising:

a base portion adapted to be coupled to a canister such that actuation of the canister to dispense a medication requires providing an actuating force on the base portion;

an interactive element coupled to the base portion that activates in a human perceivable manner, the interactive element having an activated state and a deactivated state, wherein the interactive element is in the activated state in response to an actuating force applied to the base, and wherein the interactive element returns to the same deactivated state when the actuating force is removed from the base; and actuating means for actuating the interactive element responsive to the actuating force being applied to the base portion to actuate the canister.

2. The interactive character according to claim 1, wherein the interactive element is a mechanical element that moves relative to the base portion, and wherein the actuating means comprises a mechanical linkage coupled to the mechanical element.

3. The interactive character according to claim 1, wherein the interactive element is a light that changes from the deactivated state in which light is not produced to the activated state in which light is produced responsive to actuation by the actuating means.

4. The interactive character according to claim 1, wherein the interactive element is a sound generating element that changes from the deactivated state in which no sound is produced to the activated state in which sound is produced responsive to actuation by the actuating means.

5. The interactive character according to claim 1, further comprising a spacer coupled to the second end of the holder.

6. The interactive character according to claim 1, wherein the actuating means comprises a pushrod slidably mounted within the base portion, wherein the pushrod includes a first end adapted to engage the canister and a second end adapted to engage a first portion of the interactive element.

7. An aerosol medication delivery system comprising:
1) a canister having a first end and a second end, wherein the canister is adapted to dispense a medicine from the first end;
2) a canister holder adapted to be coupled to the canister, wherein the canister is moveable relative to the canister holder between a first position to a second position, and wherein a medicine is dispensed from the canister responsive to the canister being the second position; and
3) an interactive character comprising:
   a) a base portion coupled to the second end of the canister such that movement of the canister to the second position is accomplished by applying an actuating force on the base portion,
   b) an interactive element coupled to the base portion that actuates in a human perceivable manner, the interactive element having an activated state and a deactivated state, wherein the interactive element is in the activated state in response to an actuating force applied to the base, and wherein the interactive element returns to the same deactivated state when the actuating force is removed from the base; and
   c) actuating means for actuating the interactive element responsive to the actuating force being applied to the base portion.

8. The system according to claim 7, wherein the interactive element is a mechanical element that moves relative to the base portion, and wherein the actuating means comprises a mechanical linkage coupled to the mechanical element.

9. The system according to claim 7, wherein the interactive element is a light that changes from a deactivated state in which light is not produced to an activated state in which light is produced responsive to actuation by the actuating means.

10. The system according to clam 7, wherein the interactive element is a sound generating element that changes from a deactivated state in which no sound is produced to an activated state in which sound is produced responsive to actuation by the actuating means.

11. The system according to claim 7, further comprising a spacer coupled to the second end of the holder.

12. A method using an aerosol medication delivery system comprising:

coupling a base portion of an interactive character to a canister in a metered dose inhaler;

applying an actuating force on the base portion;

automatically activating an interactive element coupled to the base portion in a human perceivable manner responsive to the application of the actuating force on the base portion such that the interactive element is in an activated state;

removing the actuating force from the base portion; and automatically deactivating the interactive element such that the interactive element returns to the same deactivated state.

13. The method of claim 12, wherein automatically activating the interactive element comprises moving a mechanical element relative to the base portion by means of a mechanical linkage having a first end operatively coupled to the canister and a second end operatively coupled to the mechanical element.

14. The method according to claim 12, wherein automatically activating the interactive element comprises changing a light from the deactivated state in which light is not produced to the activated state in which light is produced.

15. The method according to claim 12, wherein automatically activating the interactive element comprises changing a sound generating element from the deactivated state in which no sound is produced to the activated state in which sound is produced.

16. A device associated with a metered dose inhaler that includes a medication dispensing canister and a canister holder, the canister containing medication, the device comprising:

a base portion adapted to be coupled to a canister such that actuation of the canister to dispense a medication requires providing an actuating force on the base portion;

an interactive element coupled to the base portion that activates in a human perceivable manner, the interactive element having an activated state to indicate when medication is being delivered and a deactivated state to indicate when no medication is being delivered; and actuating means for actuating the interactive element responsive to the actuating force being applied to the base portion to actuate the canister.

17. A device comprising:

a base portion adapted to be coupled to a canister such that actuation of the canister to dispense a medication requires providing an actuating force on the base portion;

an interactive element coupled to the base portion that actuates in a human perceivable manner, the interactive element having an activated state and a deactivated state, wherein the interactive element is in the activated state in response to an actuating force applied to the base, and wherein the interactive element returns to the same deactivated state when the actuating force is removed from the base; and actuating means for actuating the interactive element responsive to the actuating force being applied to the base portion.

18. An aerosol medication delivery system comprising:
1) a canister having a first end and a second end, wherein the canister is adapted to dispense a medicine from the first end;
2) a canister holder adapted to be coupled to the canister, wherein the canister is moveable relative to the canister holder between a first position to a second position, and wherein a medicine is dispensed from the canister responsive to the canister being the second position; and
3) a device comprising:
   a) a base portion coupled to the second end of the canister such that movement of the canister to the second position is accomplished by applying an actuating force on the base portion,
   b) an interactive element coupled to the base portion that actuates in a human perceivable manner, the interactive element having an activated state and a deactivated state, wherein the interactive element is in the activated state in response to an actuating force applied to the base, and wherein the interactive element returns to the same deactivated state when the actuating force is removed from the base, and
   c) actuating means for actuating the interactive element responsive to the actuating force being applied to the base portion.

19. The aerosol medication delivery system as recited in claim 18, wherein the second position corresponds to the activated state and wherein the first position corresponds to the deactivated state.

20. An interactive character associated with a metered dose inhaler that includes a medication dispensing canister and a canister holder, the interactive character comprising:
a base portion adapted to be coupled to a canister such that actuation of the canister to dispense a medication requires providing an actuating force on the base portion;
an interactive element coupled to the base portion that activates in a human perceivable manner;
actuating means for actuating the interactive element responsive to the actuating force being applied to the base portion to actuate the canister;
wherein the base portion defines a first anatomical feature of the interactive character;
wherein the mechanical element defines a second anatomical feature of the interactive character;
wherein the interactive element is a mechanical element that moves relative to the base portion; and
wherein the actuating means comprises a mechanical linkage coupled to the mechanical element.

21. An interactive character associated with a metered dose inhaler that includes a medication dispensing canister and a canister holder, the interactive character comprising:
a base portion adapted to be coupled to a canister such that actuation of the canister to dispense a medication requires providing an actuating force on the base portion;
an interactive element coupled to the base portion that activates in a human perceivable manner;
actuating means for actuating the interactive element responsive to the actuating force being applied to the base portion to actuate the canister; and
wherein the base portion further comprises a pair of grasping members disposed on the base portion adapted to receive the actuating force.

22. An aerosol medication delivery system comprising:
1) a canister having a first end and a second end, wherein the canister is adapted to dispense a medicine from the first end;
2) a canister holder adapted to be coupled to the canister, wherein the canister is moveable relative to the canister holder between a first position to a second position, and wherein a medicine is dispensed from the canister responsive to the canister being the second position; and
3) an interactive character comprising:
   a) a base portion coupled to the second end of the canister such that movement of the canister to the second position is accomplished by applying an actuating force on the base portion,
   b) an interactive element coupled to the base portion that actuates in a human perceivable manner, and
   c) actuating means for actuating the interactive element responsive to the actuating force being applied to the base portion,
wherein the interactive element is a mechanical element that moves relative to the base portion,
wherein the actuating means comprises a mechanical linkage coupled to the mechanical element,
wherein the base portion defines a first anatomical feature of the interactive character, and
wherein the mechanical element defines a second anatomical feature of the interactive character.

23. An aerosol medication delivery system comprising:
1) a canister having a first end and a second end, wherein the canister is adapted to dispense a medicine from the first end;
2) a canister holder adapted to be coupled to the canister, wherein the canister is moveable relative to the canister holder between a first position to a second position, and wherein a medicine is dispensed from the canister responsive to the canister being the second position; and
3) an interactive character comprising:
   a) a base portion coupled to the second end of the canister such that movement of the canister to the second position is accomplished by applying an actuating force on the base portion,
   b) an interactive element coupled to the base portion that actuates in a human perceivable manner, and
   c) actuating means for actuating the interactive element responsive to the actuating force being applied to the base portion, and
   wherein the base portion further comprises a pair of grasping members disposed on the base portion adapted to receive the actuating force.

24. An aerosol medication delivery system comprising:
1) a canister having a first end and a second end, wherein the canister is adapted to dispense a medicine from the first end;
2) a canister holder adapted to be coupled to the canister, wherein the canister is moveable relative to the canister holder between a first position to a second position, and wherein a medicine is dispensed from the canister responsive to the canister being the second position; and 3) an interactive character comprising:
   a) a base portion coupled to the second end of the canister such that movement of the canister to the second position is accomplished by applying an actuating force on the base portion,
   b) an interactive element coupled to the base portion that actuates in a human perceivable manner,
   c) actuating means for actuating the interactive element responsive to the actuating force being applied to the base portion,
   wherein the base portion further comprises a pair of grasping members disposed on the base portion adapted to receive the actuating force, and
   wherein the actuating means comprises a pushrod slidably mounted within the base portion,
   wherein the pushrod includes a first end adapted to engage the canister and a second end adapted to engage a first portion of the interactive element.

25. A method using an aerosol medication delivery system comprising:

coupling a base portion of an interactive character to a canister in a metered dose inhaler;

applying an actuating force on the base portion;

automatically activating an interactive element coupled to the base portion in a human perceivable manner responsive to the application of the actuating force on the base portion;

wherein automatically activating the interactive element comprises moving a mechanical element relative to the base portion by means of a mechanical linkage having a first end operatively coupled to the canister and a second end operatively coupled to the mechanical element; and wherein the base portion defines a first anatomical feature of the interactive character; and wherein the mechanical element defines a second anatomical feature of the interactive character.

26. A method using an aerosol medication delivery system comprising:

coupling a base portion of an interactive character to a canister in a metered dose inhaler;

applying an actuating force on the base portion;

automatically activating an interactive element coupled to the base portion in a human perceivable manner responsive to the application of the actuating force on the base portion; and wherein applying an actuating force on the base portion comprises applying the actuating force on a pair of grasping members disposed on the base portion.

* * * * *